(12) United States Patent
Peiro Ibanez et al.

(10) Patent No.: US 12,263,075 B2
(45) Date of Patent: Apr. 1, 2025

(54) SELF-EXPANDABLE SURGICAL IMPLANT FOR CORRECTON OF CONGENITAL DIAPHRAGMATIC HERNIA

(71) Applicants: Children's Hospital Medical Center, Cincinnati, OH (US); Cristobal Abello Munarriz, Barranquilla (CO)

(72) Inventors: Jose Peiro Ibanez, Cincinnati, OH (US); Cristobal Abello Munarriz, Barranquilla (CO)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 18/513,858

(22) Filed: Nov. 20, 2023

(65) Prior Publication Data

US 2024/0090992 A1 Mar. 21, 2024

Related U.S. Application Data

(62) Division of application No. 16/824,057, filed on Mar. 19, 2020, now Pat. No. 11,819,398.

(60) Provisional application No. 62/820,395, filed on Mar. 19, 2019.

(51) Int. Cl.
*A61F 2/00* (2006.01)

(52) U.S. Cl.
CPC .... *A61F 2/0063* (2013.01); *A61F 2002/0068* (2013.01); *A61F 2002/0072* (2013.01); *A61F 2210/0057* (2013.01); *A61F 2210/0076* (2013.01); *A61F 2220/005* (2013.01); *A61F 2220/0075* (2013.01); *A61F 2250/0039* (2013.01)

(58) Field of Classification Search
CPC ............ A61F 2/0063; A61F 2002/0068; A61F 2002/0072; A61F 2210/0057; A61F 2210/0076; A61F 2220/005; A61F 2220/0075; A61F 2250/0039
See application file for complete search history.

(56) References Cited

U.S. PATENT DOCUMENTS

| | | | |
|---|---|---|---|
| 5,614,284 A | 3/1997 | Kranzier | |
| 5,725,577 A * | 3/1998 | Saxon | A61B 17/0057 623/23.72 |
| 6,174,320 B1 | 1/2001 | Kugel | |
| 6,280,453 B1 | 8/2001 | Kugel | |
| 6,746,458 B1 | 6/2004 | Cloud | |
| 6,800,082 B2 * | 10/2004 | Rousseau | A61F 2/0063 606/151 |
| 8,603,161 B2 | 12/2013 | Drews et al. | |

(Continued)

FOREIGN PATENT DOCUMENTS

EP 3025652 A1 6/2016

OTHER PUBLICATIONS

BSN Medical, Fixomull® Stretch, retrieved on Jun. 3, 2020 from https://www.bsnmedical.com/products/wound-care-vascular/category-product-search/acute-wound-care/fixation/fixomullr-stretch, 3 pages.

(Continued)

*Primary Examiner* — Jing Rui Ou
(74) *Attorney, Agent, or Firm* — Bose McKinney & Evans LLP

(57) ABSTRACT

A self-expandable double-sided surgical implant including a peripheral pocket receiving an expansion ring. The surgical implant may be used for the correction of congenital diaphragmatic hernias.

12 Claims, 6 Drawing Sheets

(56) References Cited

U.S. PATENT DOCUMENTS

| | | | |
|---|---|---|---|
| 11,819,398 | B2 | 11/2023 | Peiro Ibanez et al. |
| 2001/0049539 | A1* | 12/2001 | Rehil ............... A61F 2/0063 606/1 |
| 2003/0078602 | A1 | 4/2003 | Rousseau |
| 2003/0130745 | A1 | 7/2003 | Cherok |
| 2003/0212460 | A1 | 11/2003 | Darois |
| 2003/0212461 | A1* | 11/2003 | Vadurro ............. A61F 2/0063 623/23.72 |
| 2003/0225355 | A1 | 12/2003 | Butler |
| 2004/0087980 | A1 | 5/2004 | Ford |
| 2006/0064175 | A1 | 3/2006 | Pelissier |
| 2006/0083767 | A1* | 4/2006 | Deusch ............... A61P 43/00 424/422 |
| 2007/0299538 | A1 | 12/2007 | Roeber |
| 2010/0185219 | A1 | 7/2010 | Gertzman et al. |
| 2011/0144667 | A1* | 6/2011 | Horton ............... A61L 31/14 606/151 |
| 2016/0151136 | A1 | 6/2016 | Hamilton |

OTHER PUBLICATIONS

Cook Medical, C-Flex® Double Pigtail Ureteral Stent Set, retrieved on Jun. 3, 2020 from https://www.cookmedical.com/products/uro_cflexpigped_webds, 4 pages.

Gore Medical, Gore® Dual Mesh Biomaterial, retrieved on Jun. 3, 2020 from https://www.goremedical.com/products/dualmesh, 2 pages.

Yang EY, Allmendinger N, Johnson SM, Chen C, Wilson JM, Fishman SJ. European Journal of Pediatric Surgery Dec. 2016; 26 (6): 519-52. Neonatal thoracoscopic repair of congenital diaphragmatic hernia: selection criteria for successful outcome, 7 pages.

Tyson AF, Sola R Jr, Arnold MR, Cosper GH, Schulman AM (2017) Thoracoscopic Versus Open Congenital Diaphragmatic Hernia Repair: Single Tertiary Center Review. J Laparoendosc Adv Surg Tech A 27:1209-1216, 8 pages.

Tsao K, Lally KP (2011) Surgical Management of the Newborn with Congenital Diaphragmatic Hernia. Fetal Diagnosis and Therapy 29:46-54, 10 pages.

Tsao K, Allison ND, Harting MT, Lally PA, Lally KP (2010) Congenital diaphragmatic hernia in the preterm infant. Surgery 148:404-410, 12 pages.

Tsai J, Sulkowski J, Adzick NS, Hedrick HL, Flake AW (2012) Patch repair for congenital diaphragmatic hernia: is it really a problem? J Pediatr Surg 47:637-641, 5 pages.

Szavay PO, Obermayr F, Maas C, Luenig H, Blumenstock G, Fuchs J (2012) Perioperative outcome of patients with congenital diaphragmatic hernia undergoing open versus minimally invasive surgery. J Laparoendosc Adv Surg Tech A 22:285-289, 6 pages.

Kimber CP, Dunkley MP, Haddock G, Robertson L, Carey FA, Cuschieri A (2000) Patch incorporation in diaphragmatic hernia. J Pediatr Surg 35:120-123, 4 pages.

Bing Li, Bing Wei Chen, Qing Shou Wang, Bo Ye Wang. Thoracoscopic Repair of Diaphragmatic Hernia in Infants: A New Modification of the Technique, Eur J Pediatr Surg 2016; 26: 519-523.

Judd Boloker, David A Bateman, Jen-Tien Wung, Charles J h Stolar. Journal of Pediatric Surgery 2002, 37 (3): 357-6. Congenital diaphragmatic hernia in 120 infants treated consecutively with permissive hypercapnea/spontaneous respiration/elective repair, 10 pages.

N. Butler, A.E. Claireaux. Congenital diaphragmatic hernia as a cause of perinatal mortality. Lancet, 1 1962), pp. 659-663, 5 pages.

Clugston RD, Greer JJ. Diaphragm development and congenital diaphragmatic hernia. Seminars in Pediatric Surgery. 2007; 16(2):94-100, 7 pages.

Criss CN, Coughlin MA, Matusko N, Gadepalli SK (2018) Outcomes for thoracoscopic versus open repair of small to moderate congenital diaphragmatic hernias. J Pediatr Surg 53:635-639, 5 pages.

Shaoguang Feng, Yi Lou, Aihe Wang and Weiguang Liu. Thoracoscopic versus Open Repair of Congenital Diaphragmatic Hernia: A Systematic Review and Meta-Analysis. World Journal of Surgery and Surgical Research. 2019;2:1-6, 6 pages.

Ferreira CG, Kuhn P, Lacreuse I, Kasleas C, Philippe P, Podevin G, et al. Congenital diaphragmatic hernia: an evaluation of risk factors for failure of thoracoscopic primary repair in neonates. Journal of Pediatric Surgery. 2013;48(3):488-95, 8 pages.

Alejandro Garcia, Charles J H Stolar. Surgical Clinics of North America 2012, 92 (3): 659-68, ix. Congenital diaphragmatic hernia and protective ventilation strategies in pediatric surgery, 10 pages.

Grethel EJ, Cortes RA, Wagner AJ, Clifton MS, Lee H, Farmer DL, Harrison MR, Keller RL, Nobuhara KK (2006) Prosthetic patches for congenital diaphragmatic hernia repair: Surgisis vs Gore-Tex. J Pediatr Surg 41:29-33, 5 pages.

Inoue M, Uchida K, Otake K, Nagano Y, Mori K, Hashimoto K, Matsushita K, Koike Y, Uemura A, Kusunoki M (2016) Thoracoscopic repair of congenital diaphragmatic hernia with countermeasures against reported complications for safe outcomes comparable to laparotomy. Surg Endosc 30:1014-1019, 6 pages.

Keijzer R, Puri P. Congenital diaphragmatic hernia. Seminars in Pediatric Surgery. 2010;19(3):180-5, 6 pages.

Kuebler JF, Ure BM. Minimally invasive surgery in the neonate. Semin Fetal Neonatal Med. Jun. 2011; 16(3): 151-156, 6 pages.

Kyzer S, Sirota L, Chaimoff C (2004) Abdominal wall closure with a silastic patch after repair of congenital diaphragmatic hernia. Arch Surg 139:296-298, 5 pages.

Lacher M, St Peter SD, Laje P, Harmon CM, Ure B, Kuebler JF (2015) Thoracoscopic CDH Repair—A Survey on Opinion and Experience Among IPEG Members. Journal of Laparoendoscopic & Advanced Surgical Techniques 25:954-957, 5 pages.

Langham MR Jr, Kays DW, Ledbetter DJ, Frentzen B, Sanford LL, Richards DS (1996) Congenital diaphragmatic hernia. Epidemiology and outcome. Clin Perinatol 23:671-688, 11 pages.

Nasr A, Struijs M-C, Ein SH, Langer JC, Chiu PPL (2010) Outcomes after muscle flap vs prosthetic patch repair for large congenital diaphragmatic hernias. Journal of Pediatric Surgery 45:151-154, 4 pages.

Pérez L. Evaluación por imágenes del diafragma en el niño. Rev Chil Enf Respir 2012; 28: 236-248, 13 pages.

Quinteros A, Bancalari M. Hernia diafragmática congénita en recién nacidos. Rev Chil Pediatr 2001; 72: 19-25. 7, 7 pages.

Riehle KJ, Magnuson DK, Waldhausen JHT (2007) Low recurrence rate after Gore-Tex/Marlex composite patch repair for posterolateral congenital diaphragmatic hernia. J Pediatr Surg 42:1841-1844, 4 pages.

Romao RLP, Nasr A, Chiu PPL, Langer JC (2012) What is the best prosthetic material for patch repair of congenital diaphragmatic hernia? Comparison and meta-analysis of porcine small intestinal submucosa and polytetrafluoroethylene. J Pediatr Surg 47:1496-1500, 5 pages.

Barroso C, Correia-Pinto J (2018) Thoracoscopic repair of congenital diaphragmatic hernia: review of the results. Minerva Pediatr 70:281-28, 8 pages.

Gourlay DM, Cassidy LD, Sato TT, Lal DR, Arca MJ (2009) Beyond feasibility: a comparison of newborns undergoing thoracoscopic and open repair of congenital diaphragmatic hernias. J Pediatr Surg 44:1702-1707, 6 pages.

Qin J, Ren Y, Ma D (2019) A comparative study of thoracoscopic and open surgery of congenital diaphragmatic hernia in neonates. J Cardiothorac Surg 14:118, 7 pages.

Gasior AC, St Peter SD (2012) A review of patch options in the repair of congenital diaphragm defects. Pediatr Surg Int 28:327-333, 7 pages.

Sadler (2004), Part Two: Special Embryology, Chapter 10 Body Cavities, Formation of the Intraembryonic Cavity, pp. 211-221, 7 pages.

* cited by examiner

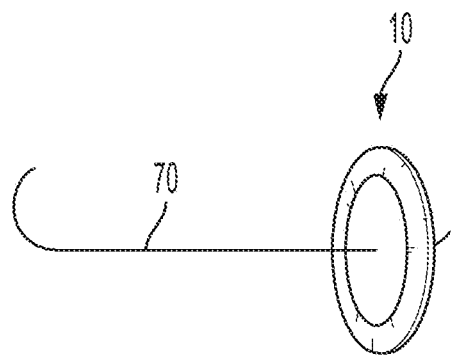
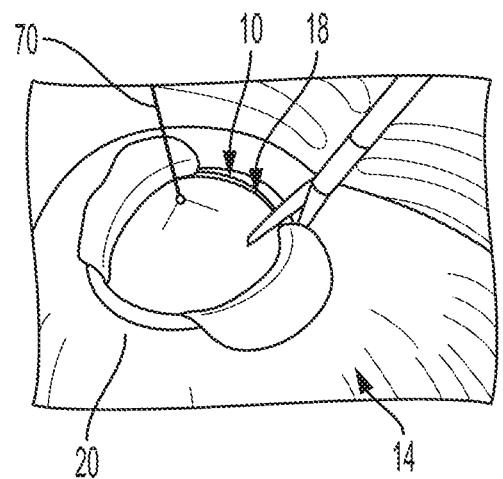
FIG. 11               FIG. 12
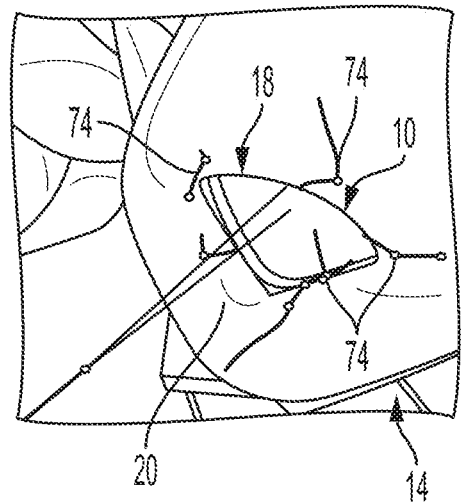
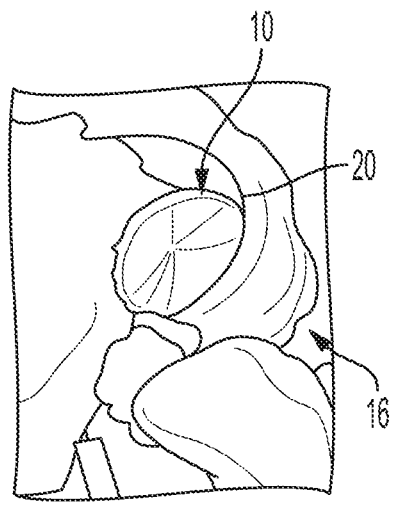
FIG. 13               FIG. 14

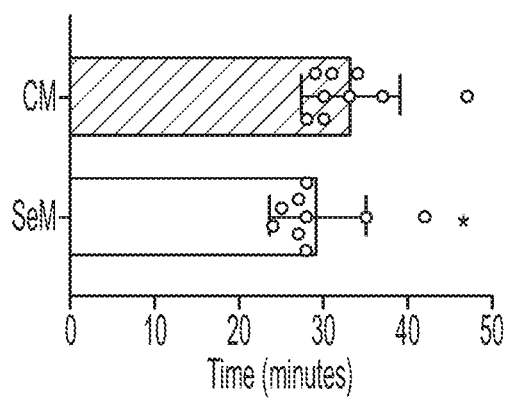
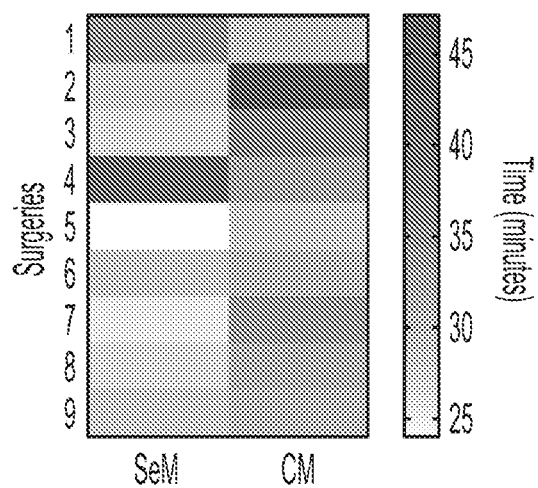
FIG. 15A    FIG. 15B
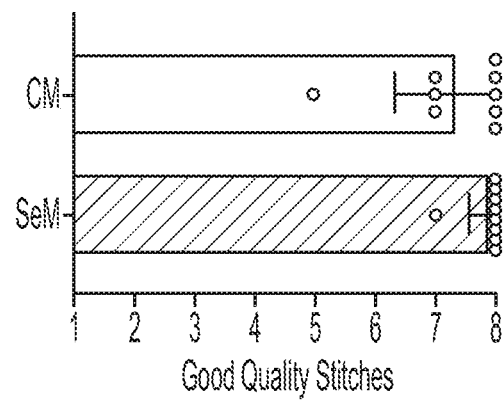
FIG. 16

SELF-EXPANDABLE SURGICAL IMPLANT FOR CORRECTON OF CONGENITAL DIAPHRAGMATIC HERNIA

CROSS-REFERENCE TO RELATED APPLICATION

The present application is a divisional of U.S. patent application Ser. No. 16/824,057, filed Mar. 19, 2020, which claims priority to U.S. Provisional Patent Application Ser. No. 62/820,395, filed Mar. 19, 2019, and U.S. Provisional Patent Application Ser. No. 62/821,504, filed Mar. 21, 2019, the disclosures of which are expressly incorporated herein by reference.

BACKGROUND AND SUMMARY OF THE DISCLOSURE

The present invention relates generally to surgical implants for repairing tissue openings and, more particularly, to such surgical implants for the thoracoscopic correction of congenital diaphragmatic hernias (CDH). Thoracoscopic repair typically involves primary or patch closure of the defect. Such surgical implants and associated methods are of particular interest to pediatric surgeons. Conventional approaches can present recurrences and technical difficulties due to the suture tension on large defects. The use of patches requires demanding thoracoscopic skills, and therefore primary closure with tight sutures is often pursued, which increases the risk of recurrence.

Embryologically, the diaphragm is formed between the eighth and tenth week of gestation, which results in the separation of the abdominal cavity and the thoracic compartment. For a congenital diaphragmatic hernia (CDH) to occur, there must be a disorder in the embryonic development of this muscle and tendon, the location and size being variable. As a consequence of this fusion defect, part of the abdominal content passes into the thorax.

Congenital diaphragmatic hernia (CDH) is a defect that occurs in 1 in 3,000 live births, of which approximately 60% occur in isolation without other congenital anomalies. As is known, congenital diaphragmatic hernias (CDH) are of two main types: Bochdalek hernias and Morgagni hernias. The most frequent diaphragmatic hernia is the Bochdalek hernia (95% of cases). A Bochdalek hernia is a congenital abnormality in which an opening exists in the infant's diaphragm, allowing normally intra-abdominal organs (particularly the stomach and intestines) to protrude into the thoracic compartment. It consists of a posterolateral defect, more frequent on the left side. Morgagni hernia, ventral and parasternal defect, is more prevalent on the right side. A hiatal hernia occurs when the gastroesophageal junction travels to the chest through the esophageal hiatus, being more frequent in adults.

The size of the diaphragmatic defect is variable and decisive in prognosis and mortality, since it clearly correlates with the degree of severity of pulmonary hypoplasia. FIG. 1 shows the location of different diaphragmatic hernias, including Bochdalek hernia 2, Morgagni hernia 4, and hiatal hernia 6. FIG. 2 illustrates different size Bochdalek hernias, such as small defects type A, intermediate type B, large type C, and at the end of the spectrum, the complete agenesis of the hemidiaphragm in type D. Illustratively, the size of the defect in Bochdalek hernias include type A of less than 3 cm, type B and C of intermediate size, and up to type D with agenesis of the diaphragmatic leaf.

The present disclosure relates to a system and associated methods for thoracoscopic surgery in newborns including a novel surgical implant or patch that facilitates the suturing process thereby minimizing the risk of injury of the underlying viscera. The illustrative surgical implant has characteristics of self-expandability and a traction central suture to stabilize the implant when it is located in the abdominal side of the patient. The surgical implant illustratively includes a folding pocket receiving an elastic ring that facilitates suturing a mesh to the diaphragmatic muscle when covering the abdominal viscera.

According to an illustrative embodiment of the present disclosure, surgical implant for repairing a tissue opening includes a body having a proximal member, a distal member coupled to the proximal member, and a peripheral pocket. The peripheral pocket is defined by a reentrant outer edge of the distal member extending around an outer edge of the proximal member. A resilient ring is received within the peripheral pocket and is configured to apply tension to the body.

According to a further illustrative embodiment of the present disclosure, a method of forming a surgical implant includes the steps of providing a thoracic member having a proximal surface and a distal surface, providing an abdominal member having a proximal surface and a distal surface, and positioning the distal surface of the thoracic member adjacent to the proximal surface of the abdominal member. The method further includes the steps of folding an outer rim of one of the abdominal member and the thoracic member over an outer edge of the other of the thoracic member and the abdominal member to define a reentrant lip, and securing the thoracic member to the abdominal member by the reentrant lip. The method further includes the steps of defining a peripheral pocket with the reentrant lip, and inserting a support ring within the peripheral pocket.

According to another illustrative embodiment of the present disclosure, a method of attaching a surgical implant to a diaphragmatic hernia includes the steps of providing a surgical implant including a body having a proximal member, a distal member coupled to the proximal member, a peripheral pocket defined by a reentrant outer rim of the distal member extending around an outer edge of the proximal member, and a support ring received within the peripheral pocket and configured to apply tension to the body, and folding the surgical implant. The method further includes the steps of passing the folded surgical implant from a thoracic compartment, through a diaphragmatic rim, and into the abdominal cavity, and expanding the support ring to apply tension to the body of the surgical implant. The method further includes the steps of pulling a central suture coupled to the body to stabilize the surgical implant against the diaphragmatic rim, and suturing the body of the surgical implant to the diaphragmatic rim.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 11 is a perspective view of the illustrative surgical implant of FIG. 3, including a central placement suture;

FIG. 12 is a perspective view showing the central suture providing traction for stability against a diaphragmatic rim;

FIG. 13 is a perspective view of the thoracic side of the illustrative surgical implant of FIG. 3 in situ;

FIG. 14 is a perspective view of the abdominal side of the illustrative surgical implant of FIG. 3 in situ;

FIG. 15A is a graph showing surgical time for representative surgical implant placements;

FIG. 15B is a heat map showing surgical time for representative surgical implant placements;

FIG. 16 is a graph showing mean of good quality stitches per representative surgical implant, with whiskers illustrating standard deviation;

DETAILED DESCRIPTION OF THE DRAWINGS

Figure 1:
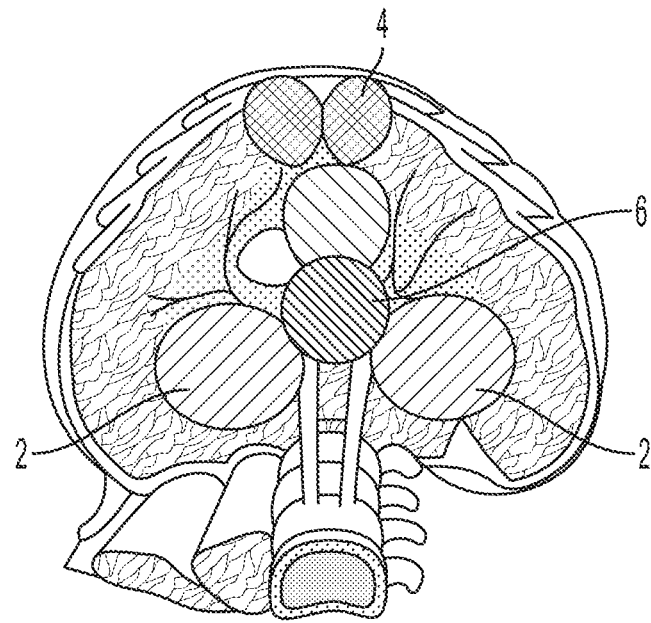
FIG. 1 is a cross-sectional view of different illustrative diaphragmatic hernias.
Figure 2:
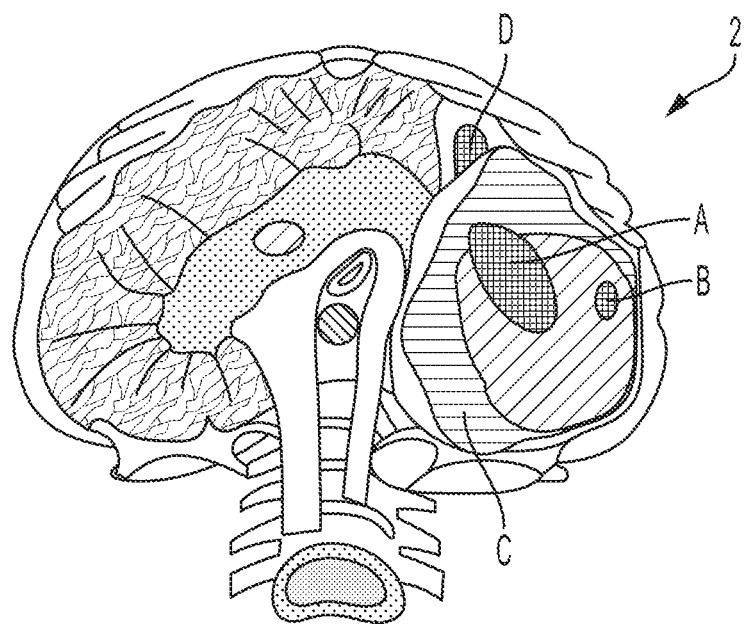
FIG. 2 is a cross-sectional view of different illustrative Bochdalek type congenital diaphragmatic hernias (CDH)

For the purposes of promoting an understanding of the principles of the present disclosure, reference will now be made to the embodiments illustrated in the drawings, which are described herein. The embodiments disclosed herein are not intended to be exhaustive or to limit the invention to the precise form disclosed. Rather, the embodiments are chosen and described so that others skilled in the art may utilize their teachings. Therefore, no limitation of the scope of the claimed invention is thereby intended. The present invention includes any alterations and further modifications of the illustrated devices and described methods and further applications of principles in the invention which would normally occur to one skilled in the art to which the invention relates.

Figure 3:
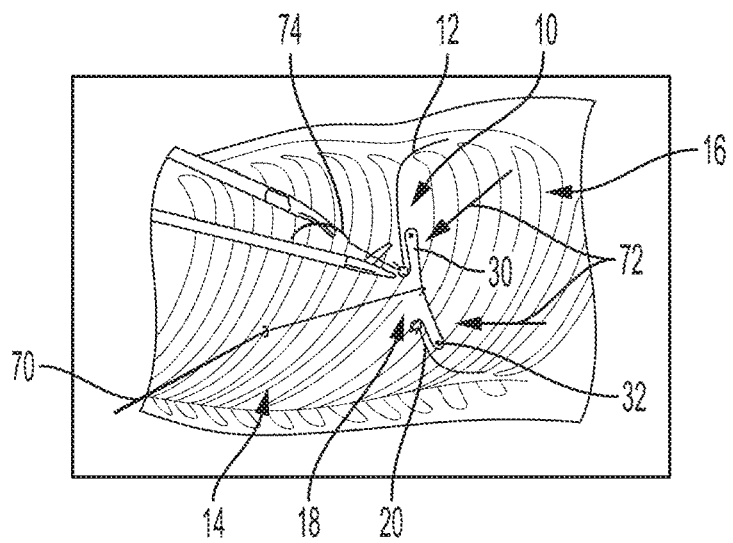
FIG. 3 is a cross-sectional view of a surgical implant according to an illustrative embodiment of the present disclosure placed in a diaphragmatic opening.

With reference to FIG. 3, an illustrative surgical implant 10 is configured to be supported by a diaphragm 12 intermediate a thoracic compartment 14 and an abdominal cavity 16. More particularly, the implant 10 is supported within a defect, illustratively a diaphragmatic opening 18 defined by a diaphragmatic rim 20. In the following detailed description, the surgical implant 10 may also be referred to as a patch or self-expandable mesh (SeM).

With reference to FIGS. 3-10B, the surgical implant 10 illustratively includes a body 22 including a proximal member 24 coupled to a distal member 26. A reentrant outer lip 28 of the distal member 26 defines a peripheral pocket 30 receiving a support ring 32 thereby expanding the surgical implant 10.

Figure 4:
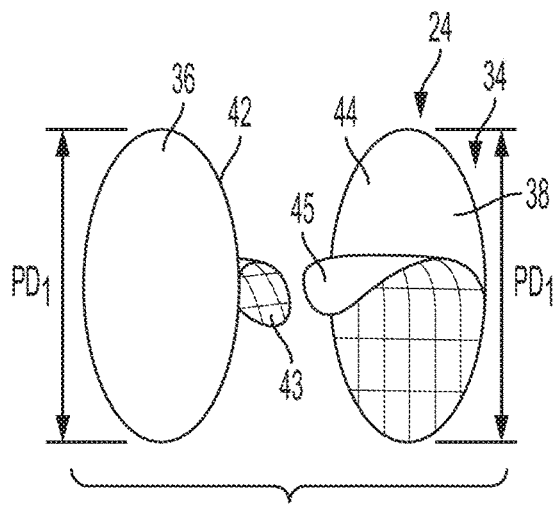
FIG. 4 is an exploded perspective view of a thoracic member of the illustrative surgical implant of FIG. 3.
Figure 5:
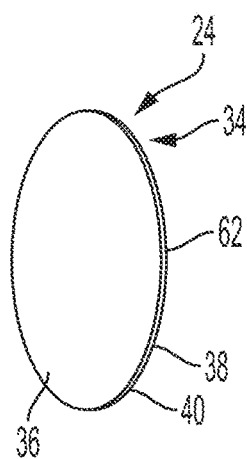
FIG. 5 is a perspective view of the thoracic member of FIG. 4.

With reference to FIGS. 4 and 5, the proximal member 24 is illustratively a circular thoracic member 34 including a first or proximal mesh layer 36 coupled to a second or distal mesh layer 38. An adhesive layer 40 illustratively couples the first mesh layer 36 to the second mesh layer 38. The first mesh layer 36 and the second mesh layer 38 are illustratively circular disks having a proximal outer diameter ($PD_1$). In an illustrative embodiment, the proximal outer diameter ($PD_1$) is approximately 6 cm.

The proximal member 24 is illustratively formed of a mesh material such as a synthetic biocompatible material. More particularly, each mesh layer 36 and 38 of the proximal member 24 are illustratively formed of a stretchable nonwoven polyester with a hypoallergenic polyacrylate adhesive surface 42 and 44, respectively. Releasable liners 43 and 45 may cover the adhesive surfaces 42 and 44, respectively, until assembled into the proximal member 24. In one illustrative embodiment, the mesh layers 36 and 38 may be formed from Fixomul® Stretch dressing material (Ref. 70022-00 available from BSN Medical GmbH of Hamburg, Germany). The proximal member 24 may be adapted to any suitable material, synthetic or biocompatible. For example, a polytetrafluoroethylene (ePTFE) material may be used for the proximal member 24 (such as Dualmesh® Biomaterial, available from W.L. Gore & Associates of Flagstaff, Arizona).

During assembly of the thoracic member 34, two circular mesh layers 36 and 38 of substantially equal outer diameters ($PD_1$) (illustratively, 6 cm each) are positioned with their adhesive surfaces 42 and 44 facing one another following removal of the liners 43 and 45. The adhesive surfaces 42 and 44 are then brought into contact with each other such that the surfaces 42 and 44 together define the adhesive layer 40 (FIG. 4) for securing the first mesh layer 36 with the second mesh layer 38.

Figure 6:
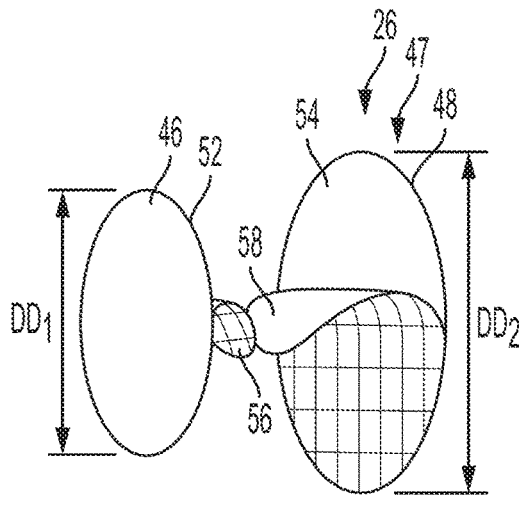
FIG. 6 is an exploded perspective view of an abdominal member of the illustrative surgical implant of FIG. 3.
Figure 7:
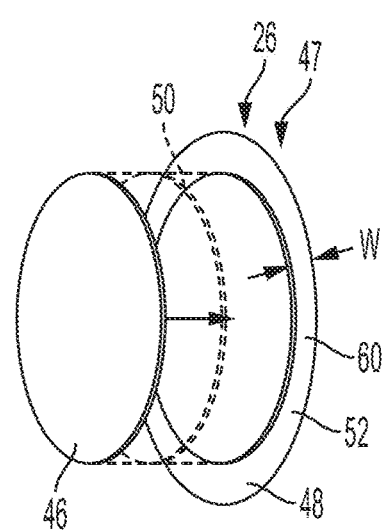
FIG. 7 is a perspective view of the abdominal member of FIG. 6.

With reference to FIGS. 6 and 7, the distal member 26 is illustratively a circular abdominal member 47 including a first or proximal mesh layer 46 coupled to a second or distal mesh layer 48. An adhesive layer 50 illustratively couples the first mesh layer 46 and the second mesh layer 48. The first mesh layer 46 illustratively has a first distal outer diameter ($DD_1$), and the second mesh layer 48 illustratively has a second distal outer diameter ($DD_2$). Illustratively, the second distal outer diameter ($DD_2$) is greater than the first distal outer diameter ($DD_1$), thereby defining an outer rim 60. In an illustrative embodiment, the first distal outer diameter ($DD_1$) is approximately 6 cm, while the second distal outer diameter ($DD_2$) is approximately 8 cm. As such, the outer rim 60 has a width (W) of approximately 1 cm.

The distal member 26 is illustratively formed of a mesh material such as a synthetic biocompatible material. More particularly, each mesh layer 46 and 48 of the distal member 26 are illustratively formed of a stretchable nonwoven polyester with a hypoallergenic polyacrylate adhesive surface 52 and 54, respectively. Releasable liners 56 and 58 may cover the adhesive surfaces 52 and 54, respectively, until assembled into the distal member 26. In one illustrative embodiment, the mesh layers 46 and 48 may be formed from Fixomul® Stretch dressing material (Ref. 70022-00 available from BSN Medical GmbH of Hamburg, Germany).

The distal member 26 may be formed of any kind of synthetic or biocompatible material, if it complies with the functional features including sufficient resiliency to be compressed and subsequently expanded by the support ring 32 received within the pocket 30. For example, a polytetrafluoroethylene (ePTFE) material may be used for the distal member 26 (such as Dualmesh® Biomaterial, available from W.L. Gore & Associates of Flagstaff, Arizona).

During assembly of the distal member 26 as shown in FIGS. 8-10B, two circular mesh layers 46 and 48 of different outer diameters ($DD_1$) and ($DD_2$)(illustratively, 6 cm and 8 cm, respectively) are positioned with their adhesive surfaces 52 and 54 facing one another following removal of the liners 56 and 58. The adhesive surfaces 52 and 54 are then brought into contact with each other such that the surfaces 52 and 54 together define the adhesive layer 50 (FIGS. 6 and 7) for securing the first mesh layer 46 with the second mesh layer 48.

As noted above, the surgical implant 10 can be formed of a wide variety of synthetic biocompatible materials, if it complies with the required functional features. For the creation of the proximal member 24, two circular mesh layers 36 and 38 of 6 cm outer diameter are pasted on top of each other, with their adhesive surfaces 42 and 44 facing one another (FIGS. 4 and 5). For the distal member 26, two circular mesh layers 46 and 48 of 6 and 8 cm outer diameters are pasted on top of each other as described for the proximal member 24 (FIGS. 6 and 7).

Figure 8:
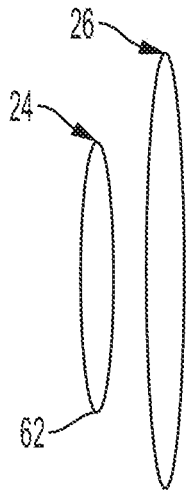
FIG. 8 is an exploded perspective view of the thoracic member and the abdominal member of the illustrative surgical implant of FIG. 3.
Figure 9A:
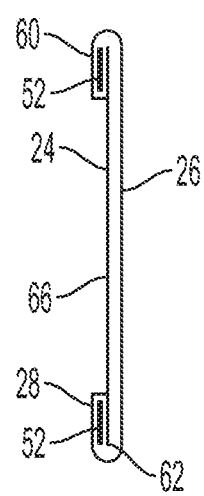
FIGS. 9A-9C are cross-sectional views, in partial schematic, showing assembly steps of the illustrative surgical implant of FIG. 3.
Figure 9B:
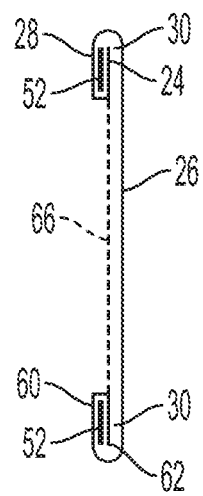
Figure 9C:
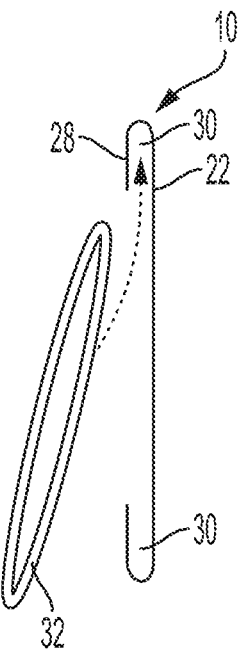
Figure 10A:
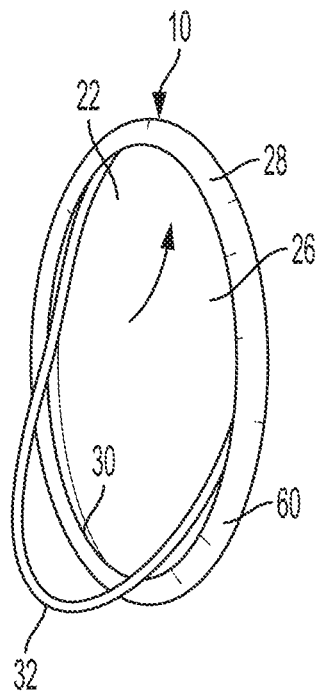
FIGS. 10A and 10B are perspective views showing the support ring inserted within the peripheral pocket of the illustrative surgical implant of FIG. 3.
Figure 10B:
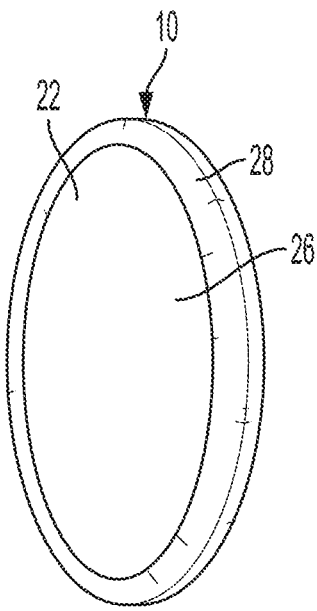

Next, the proximal member 24 and the distal member 26 are approached to each other (FIG. 8). The 2 cm difference between the between the two members 24 and 26 define the outer rim 60 having a width (W) of 1 cm. The outer rim 60 is folded over an outer edge 62 of the proximal member 24 to define the reentrant outer lip 28. The adhesive surface 52 on the mesh layer 48 of the distal member 26 secures the reentrant outer lip 28 to the mesh layer 36 of the proximal member 24 to create the pocket 30 (FIGS. 9A-9C). Afterwards, a center 66 of the proximal member 24 is cut away to open access to the pocket 30 (FIG. 9B) where the support ring 32 is received (FIGS. 9C-10B).

The support ring 32 is illustratively a semi-rigid annular member having a shape memory, so the surgical implant 10 will remain expanded (FIG. 9C), illustratively to an outer diameter equal to $DD_1$ (e.g., approximately 6 cm). Illustratively, the support ring 32 may be formed of a resilient polymer, such as an elastomer and/or silicone. In one illustrative embodiment, the support ring 32 is formed from the stent positioner of a pigtail ureteral stent (Ref. 036308 available from Cook Medical of Bloomington, Indiana), by joining the opposing ends with n-butyl-2-cyanoacrylate adhesive (Ref. 1050052 available from B Braun Histoacryl® of Bethlehem, Pennsylvania).

A central placement suture 70 is illustratively secured in the center of the distal member 26 of the surgical implant 10 that allows traction from the thoracic compartment 14 against the diaphragmatic rim 20, providing in situ stability for the suturing process (FIGS. 11-14). Illustratively, the central placement suture 70 is a 20 cm 2/0 silk suture.

An illustrative method of attaching the surgical implant 10 to a diaphragmatic hernia 18 may utilize known minimally invasive surgical procedures, such as videotorascopic techniques. Illustratively, the method includes an initial step of compressing, illustratively folding, the surgical implant 10. More particularly, the surgical implant 10 is collapsed or rolled for passing from the thoracic compartment 14, through the opening 18 defined by the diaphragmatic rim 20, and into the abdominal cavity 16. A conventional surgical instrument, such as a trocar, may be used to position the surgical implant 10. More particularly, after having reduced the herniated intestine, the surgical implant 10 is moved to the abdominal cavity 16 through the defect 18 with the support ring 32 providing for expansion of the body 22.

The surgical implant 10 is configured to self-expand as a result of the support ring 32 received within the pocket 30. Once the support ring 32 is expanded in the abdominal side of the defect 18, the body 22 remains deployed in close contact with the diaphragmatic rim 20 by positive pressure of the abdominal cavity 16 and the negative pressure of the thoracic compartment 14 (the pressure differential being represented by arrows 72 in FIG. 3).

Once the surgical implant 10 is adequately positioned within the abdominal cavity 16, the central placement suture 70 is illustratively pulled axially toward the thoracic compartment 14 through a surgical instrument (e.g., a trocar) to assist in keeping the surgical implant 10 in place during the suturing process. The surgical implant 10 is illustrated as being positioned below the diaphragmatic rim 20 supported on the edges of the defect 18 and enhanced by external traction of the central placement suture 70.

Conventional sutures or stitches 74 are illustratively used to secure the body 22 of the surgical implant 10 to the diaphragm 12. More particularly, stitches 74 may secure the pocket 30 and/or support ring 32 to the diaphragmatic rim 20. The suturing can be performed using intracorporeal or extracorporeal knot-tying technique. Illustratively, at least 8 equidistant interrupted stitches 74 with at least 3 throws per knot are provided to secure the surgical implant 10. It should be appreciated that the number of stitches 74 can vary with the size of the surgical implant 10 and/or the defect 18. After the suturing process is complete, the central placement suture 70 can be cut away. It should be appreciated that the support ring 32 may remain within the pocket 30 following the suturing step, or be removed from the pocket 30 depending upon the type and placement of the stitches 74 relative to the surgical implant 10.

The surgical implant 10 isolates and protects all the abdominal viscera. The proximity of the free edge of the pocket 30 in the thoracic side to the diaphragmatic margins allows an easy and precise suture with continuous or interrupted stitches 74. The distal mesh 26 forges a pocket 30 around the ring 32, embracing it. The margins of that pocket 30 in his thoracic side will be facing the diaphragmatic rim 20 to allow an easy and precise suture. Eventually, the support ring 32 will give a safe surface below every stitch to avoid inadvertent injuries of the underlying viscera. Finally, the surgical implant 10 is essentially stable due to a traction central placement suture 70 that keeps the implant 10 in close contact with the diaphragmatic rim 20 (FIG. 3).

An inanimate model for the thoracoscopic repair of congenital diaphragmatic hernia (CDH) was used to recreate the surgical technique. In the following description, different variables are compared for both the surgical implant 10 of the present disclosure (identified as self-expanding mesh (SeM)) and known patches (identified as conventional mesh (CM)). Illustratively, nine CDH cases were repaired with each type of mesh (n=18 CDH cases) in an inanimate model of the disease by experiences pediatric surgeons.

Quantitative and qualitative data results are expressed as mean+/−standard deviation (SD). For the comparison of not normal distributed groups, differences between means were compared using Mann-Whitney test. Statistical analysis and figures were made using the Prism 8 package (available from Graphpad Software Inc. of La Jolla, California), and p value<0.05 was considered statistically significant.

With reference to FIGS. 15A and 15B, the variable of surgical time for placement of surgical implant is assessed in minutes from its introduction through the port of the surgical instrument until its complete suture. FIG. 15A shows the average surgical time taken for each mesh with distribution and standard deviation for nine placements. The surgical time taken for SeM placement was significantly lower (29.3±5.6 minutes) compared to 33.2±5.9 minutes for the CM (*p≤0.05, Mann-Whitney). The differences in time used to place and suture the different implants can be observed in the heatmap of FIG. 15B.

With reference to FIG. 16, the variable of quality of the suturing process is assessed by quantifying the number of good quality knots (with at least three throws per knot, tight enough to the implant and the diaphragmatic rim), and the occurrence of an adverse event during the suturing such as bowel injury, diaphragmatic rips or large gaps between knots. FIG. 16 shows the mean of good quality stitches/knots per surgical implant with whiskers showing standard deviation. The number of good quality stitches/knots per mesh was in average 7.9±0.3 for SeM and 7.3±1 for CM, considering that the number of stitches placed per mesh was 8. The percentage of surgeries in which all the knots were good quality (scoring 8 out of 8) were 55.6% for CM and 88.8% for SeM.

The adverse events occurring during the suturing process were 1 for the SeM (diaphragmatic rip n=1) and 7 for the CM (bowel injury n=2, diaphragmatic rip n=2, and large gaps between knots n=3).

Figure 17A:
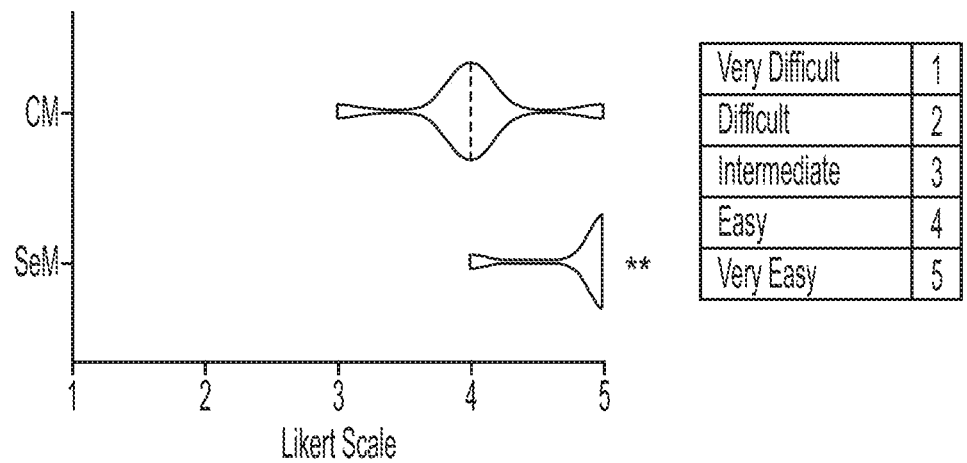
FIG. 17A is a graph showing the level of difficulty for representative surgical implant placements.
Figure 17B:
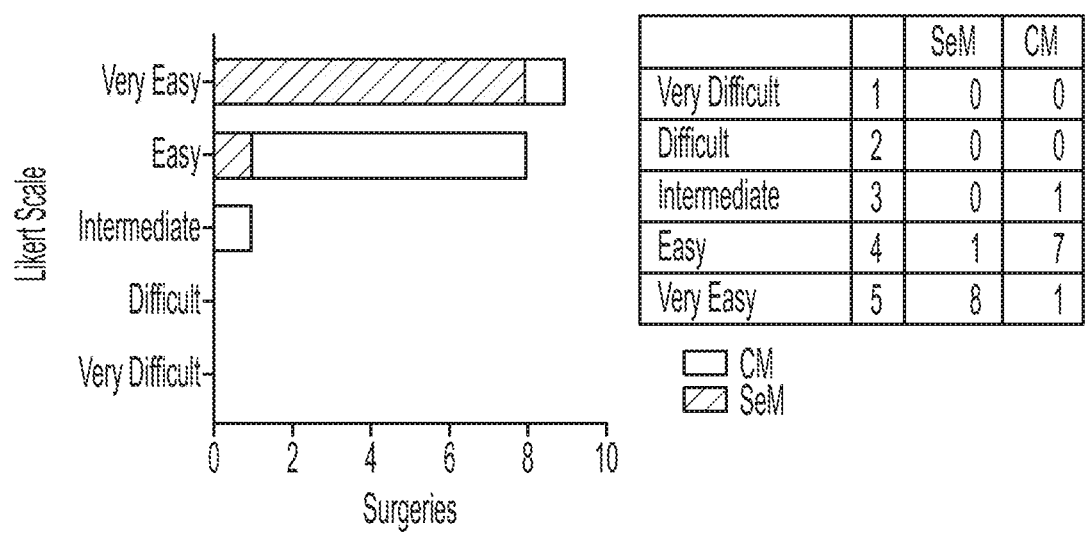
FIG. 17B is a graph of the Likert scale for representative surgical implant placements.

FIGS. 17A and 17B show the assessment of the level of difficulty of the surgical procedure using a five-point Likert scale (Very Easy, Easy, Intermediate, Difficult and Very Difficult). FIG. 17A is a Violin plot for each surgical implant's Likert scale and data distribution. The level of difficulty reported for each procedure using the five-points Likert scale were 4.8±0.3 and 4.0±0.5 for the SeM and CM respectively (p≤0.001, Mann-Whitney) (FIG. 17A). FIG. 17B shows the Likert scale for each surgical implant. SeM placement was reported to be Very easy (n=8) and Easy (n=1), and for the CM was Very easy (n=1), Easy (n=7) and Intermediate (n=1) (FIG. 17B**).

In summary, nine cases of CDH were repaired with each type of implant (SeM and CM). The total duration of the procedure was shorter when using the self-expandable mesh (SeM) 10 when compared to the conventional mesh (CM) (p≤0.05). The level of difficulty was reported to be lower for the self-expandable mesh (SeM) 10 (p≤0.001). The number of good quality knots was higher and adverse events were less common for the self-expandable mesh (SeM) 10, with no visceral injury observed.

The surgical implant of the present disclosure in the form of a stabilizing self-expanding mesh (SeM) offers a safe and ergonomic performance for the thoracoscopic repair of congenital diaphragmatic hernia (CDH) facilitating the surgical technique, especially for large defects where the primary closure can lead to recurrences. The main advantages of this surgical implant are that it keeps the viscera isolated into the abdomen while offering a flap on the thoracic side for suturing in a comfortable and practical fashion, minimizing the risk of visceral injury and saving surgical time that is especially precious in patients with pulmonary hypertension. The quality of the suturing process is superior with this novel surgical implant system and although in this surgical model is not possible to follow-up for the analysis of long term results, it would be interesting to study in animal models if these immediate benefits observed in the surgery, have some impact in the recurrence of the disease. The surgical implant of the present disclosure is synthetic but is customizable and could be made with biological materials as well.

This novel mesh has been created to facilitates the thoracoscopic repair of the neonatal CDH. It has characteristics of self-expandability due to the presence of a semi-rigid ring. Once the ring is expanded in the abdominal side of the defect, it remains deployed in close contact with the diaphragmatic rim facilitated by the positive pressure of the abdominal cavity and the negative pressure of the thoracic compartment. The mesh itself will isolate and protect the viscera in the abdominal compartment, minimizing the risk of injury.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative system and method, and illustrated examples shown and described. Accordingly, departures may be made from such details without departing from the scope or spirit of the invention.

The invention claimed is:

1. A method of attaching a surgical implant to a diaphragmatic hernia comprising the steps of:
    providing a surgical implant including a body having a proximal member, a distal member coupled to the proximal member, a peripheral pocket defined by a reentrant outer lip of the distal member extending around an outer edge of the proximal member, and a support ring received within the peripheral pocket and configured to apply tension to the body;
    folding the surgical implant;
    passing the folded surgical implant from a thoracic compartment, through a diaphragmatic rim, and into an abdominal cavity;
    expanding the support ring to apply tension to the body of the surgical implant;
    pulling a central suture coupled to the body to stabilize the surgical implant against the diaphragmatic rim; and
    suturing the body of the surgical implant to the diaphragmatic rim.

2. The method of claim 1, further comprising the step of cutting the central suture following the suturing step.

3. The method of claim 1, wherein the body is a mesh formed of a stretchable nonwoven polyester or polytetrafluoroethylene material.

4. The method of claim 1, wherein the support ring is formed of a resilient polymer.

5. The method of claim 1, wherein the folding step comprises rolling the surgical implant for insertion through a trocar.

6. A method of attaching a surgical implant to a diaphragmatic hernia comprising the steps of:
    providing a surgical implant including a body having a thoracic member, an abdominal member coupled to the thoracic member, a peripheral pocket defined by a reentrant outer lip of one of the abdominal member and the thoracic member extending around an outer edge of the other of the thoracic member and the abdominal member, and a support ring received within the peripheral pocket and configured to apply tension to the body;
    folding the surgical implant;
    passing the folded surgical implant from a thoracic compartment, through a diaphragmatic rim, and into an abdominal cavity;
    expanding the support ring to apply tension to the body of the surgical implant; and suturing the body of the surgical implant to the diaphragmatic rim.

7. The method of claim 6, further comprising the step of stabilizing the surgical implant against the diaphragmatic rim.

8. The method of claim 7, wherein the stabilizing step includes pulling a central suture coupled to the body.

9. The method of claim 8, further comprising the step of cutting the central suture following the suturing step.

10. The method of claim 6, wherein the body is a mesh formed of a stretchable nonwoven polyester or polytetrafluoroethylene material.

11. The method of claim 6, wherein the support ring is formed of a resilient polymer.

12. The method of claim 6, wherein the folding step comprises rolling the surgical implant for insertion through a trocar.

\* \* \* \* \*

UNITED STATES PATENT AND TRADEMARK OFFICE
CERTIFICATE OF CORRECTION

PATENT NO. : 12,263,075 B2
APPLICATION NO. : 18/513858
DATED : April 1, 2025
INVENTOR(S) : Jose Peiro Ibanez and Cristobal Abello Munarriz It is certified that error appears in the above-identified patent and that said Letters Patent is hereby corrected as shown below:

On the Title Page

Item (62), "Related U.S. Application Data" after "Provisional application No. 62/820,395, filed on March 19, 2019." insert:
--Provisional application No. 62/821,504, filed on March 21, 2019.--

Signed and Sealed this
Nineteenth Day of August, 2025

Coke Morgan Stewart
*Acting Director of the United States Patent and Trademark Office*